United States Patent [19]

Hemmi et al.

[11] Patent Number: 5,886,173

[45] Date of Patent: Mar. 23, 1999

[54] METALLATION OF MACROCYCLES WITH 2,4-DICARBONYL-METAL COMPLEXES

[75] Inventors: Gregory W. Hemmi, Sunnyvale; Miguel Rosingana, San Francisco, both of Calif.

[73] Assignee: Pharmacyclics, Inc., Sunnyvale, Calif.

[21] Appl. No.: 903,121

[22] Filed: Jul. 30, 1997

[51] Int. Cl.$^6$ .................... C07D 487/22; C07D 257/00
[52] U.S. Cl. .................... 540/472; 540/145; 540/465; 534/11; 534/15
[58] Field of Search ............ 534/11, 15; 540/145, 540/472, 465

[56] References Cited

U.S. PATENT DOCUMENTS

| | | | |
|---|---|---|---|
| 4,935,498 | 6/1990 | Sessler et al. | 534/15 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1994 | Sessler et al. | 204/157.5 |
| 5,591,422 | 1/1997 | Hemmi et al. | 424/9.362 |

FOREIGN PATENT DOCUMENTS

WO 95/21845   11/1995   WIPO .

OTHER PUBLICATIONS

R.G. Lauffer *Magn. Reson Q.* (1990) 6: 2.
C.F. Meares et al. *Br. J. Cancer Suppl.* (1990) 10: 21.
G. Jori et al. *J. Photochem. Photobiol. B* (1990) 6: 93.
S.W. Young et al. *Proc. Nat. Acad. Sci. U.S.A.* (1996) 93: 6610.
S.W. Young et al. *Invest. Radiol.* (1996) 31: 280.
J.L. Sessler et al. *Accounts of Chemical Research* (1994) 27: 43.
S.W. Young et al. *Invest. Radiol.* (1996) ??L 353.
J.F. Desreux *Lanthanide Probes in Life, Chemical and Earth Sciences*. Theory and Practice, Bunzli, J.—C.G. Ed., Elsevier, New York (1989) pp. 43–64.

*Primary Examiner*—Mukund J. Shah
*Assistant Examiner*—Pavanaram K Sripada
*Attorney, Agent, or Firm*—Townsend and Townsend and Crew

[57] ABSTRACT

A method has been developed which utilizes a metal-2,4-dicarbonyl complex as an organic solvent soluble metal ion source in the metallation of polyazamacrocycles including porphyrins, expanded porphyrins and porphyrinoid compounds. Use of a metal ion source which is soluble in the metallation reaction medium produces significantly higher yields of a measurably purer product than is achieved using an insoluble or only sparingly soluble metal salt as in the prior art. Additionally, because the metallation can be performed in relatively concentrated mixtures, the reaction times are dramatically shorter and the amount of waste produced is less than when simple metal salts serve as the metal ion source. Further, use of the soluble metal-2,4-dicarbonyl complex simplifies the purification protocol required for the metallated expanded porphyrin.

20 Claims, No Drawings

METALLATION OF MACROCYCLES WITH 2,4-DICARBONYL-METAL COMPLEXES

FIELD OF THE INVENTION

This invention relates to the metallation of macrocyclic ligands, particularly porphyrinoid macrocycles such as texaphyrins, in organic solvents using organic soluble 2,4-dicarbonyl complexes of metal ions.

BACKGROUND OF THE INVENTION

Polyazamacrocyclic metal complexing agents such as the polyazamacrocycles (e.g., 1,4,7,10-tetraazacyclododecane and its derivatives, "TACD"), porphyrins (e.g., tetraphenylporphine, "TPP") and porphyrinoid compounds are of interest as both therapeutic and diagnostic agents. For example, derivatives of TACD complexed with paramagnetic metal ions have been used as contrast enhancing agents for magnetic resonance imaging (MRI) to enhance the diagnostic yield of images obtained with this technique. See, for example, Lauffer, R. B., *Magn. Reson. Q.* 1990:6, 2 and references therein. Metallated tetraazamacrocycles have also been used therapeutically and are particularly useful in cancer chemotherapy. See, for example, Meares, C. F., et al., *Br. J. Cancer Suppl.* 1990:10, 21.

Metalloporphyrins are of interest as photosensitizing agents for tumor therapy. See, for example, Jori, G., et al., *J. Photochem. Photobiol.* B 1990:6, 93. Additionally, porphyrins which are metallated with paramagnetic metal ions such as gadolinium (III) have been used as MRI contrast enhancing agents. For example, see Lyon, R. C., et al., *Magn. Reson. Med.* 1987:4, 255. The gadolinium complexes of a class of porphyrinoids or expanded porphyrins known as "texaphyrins" have proven of particular interest in imaging applications. For example, see, Young, S. W., et al., *Proc. Nat. Acad. Sci. U.S.A.* 1996:93, 6610 and Young, S. W., et al., *Invest. Radiol.* 1996:31, 280. In addition, the lutetium (III) complexes of texaphyrins are useful in photodynamic therapy applications. Woodburn, K. W., et al., *J. Clin. Laser Med. Surg.* 1996:14, 343; Young, S. W., et al., *Photochem. Photobiol.* 1996:63, 892.

The texaphyrins are aromatic pentadentate macrocyclic "expanded porphyrins" that are useful as magnetic resonance imaging (MRI) contrast agents, radiosensitizers, chemosensitizers and as agents in photodynamic therapy (PDT). As used herein, the term "expanded porphyrins" denotes a tripyrrolic pentaazaporphyrinoid compound. A texaphyrin is an aromatic benzannulene containing both $18\pi$- and $22\pi$-electron delocalization pathways. See, for example, Sessler, J. L., et al., *Accounts of Chemical Research* 1994:27, 43. Texaphyrins and water-soluble texaphyrins and methods of preparation have been described in U.S. Pat. Nos. 4,935,498, 5,252,720, 5,256,399, 5,272,142, 5,292,414 and 5,599,923, all of which are incorporated herein by reference.

The metal complexes of aromatic texaphyrins are produced by the oxidation and metallation of a reduced non-aromatic macrocycle precursor (the "$sp^3$" compound). The resulting reaction mixture contains free (uncomplexed) metal ions in solution together with the texaphyrin-metal complex product. The free metal ions must be removed from the reaction mixture because they can have a deleterious effect on biolocalization (reducing efficacy) or on stability, and they can interfere with use of the texaphyrin-metal complex in any of its various functions. More importantly, the free metal ion can render texaphyrin-metal complex preparations toxic in vivo.

In current practice, texaphyrins are metallated using a mixture of the macrocycle and a metal salt in an organic solvent such as methanol. When the metal salt is only sparingly soluble in the organic solvent, the metallation reaction is slow, the rate-limiting step being the dissolution of the metal salt. To offset the low solubility of the metal salt, it is necessary to use substantial volumes of the organic reaction solvent, a stoichiometric excess of the metal salt and long reaction times. As the reaction is scaled up, large amounts of both solvent and metal salt are required. This quickly passes from unwieldy to impractical. As the required amounts of solvent and metal salt increase, there is a need for specialized reaction vessels, the amount of chemical waste generated is increased, and purification of the metallated macrocycle becomes burdensome.

Production of large volumes of waste to produce relatively small amounts of product is undesirable due to both the expense of the starting chemicals and the expense associated with disposing of the chemical waste. Further, there is a growing sensitivity to the long-term environmental impact associated with disposal of chemical waste in landfills or by incineration. Thus, both economic and ecological concerns dictate that the amount of waste chemicals produced by a reaction sequence be minimized whenever possible.

The current reaction sequence affords yields of the desired macrocycle-metal complex which are low, often no more than 20–30% of the theoretical yield. Further, the required reaction times are lengthy (e.g., 29 h). Purification protocols must be used to remove from the reaction mixture the sparingly soluble unreacted metal salt, which is present in substantial excess, thereby increasing the time and number of steps required to isolate the desired product. Thus, a method for metallating expanded porphyrins, such as texaphyrins, which affords good yields of the desired product, after a short reaction time and a simple purification protocol would be quite desirable. If such a method could also reduce solvent and metal salt use it would constitute a substantial advance in this field. This invention provides such a method.

SUMMARY OF THE INVENTION

It has now been discovered that an intermediate metal-2, 4-dicarbonyl complex which is soluble in an organic solvent can be used to metallate macrocyclic ligands. The intermediate 2,4-dicarbonyl complex is formed by the reaction between a metal ion derived from a metal salt and a 2,4-dicarbonyl compound. Once formed, the intermediate metal-2,4-dicarbonyl complex is reacted with the macrocyclic ligand in an organic solvent. Because the metal-2,4-dicarbonyl complex has a greater solubility in organic solvents than the precursor metal salt, it is possible to conduct the metallation of the macrocycle at higher concentrations than is possible with the uncomplexed metal salt, thus reducing solvent use. The enhanced solubility of the metal ion source and the increased concentration of reactants result in shorter reaction times than are necessary when the uncomplexed metal salt is used as the metal ion source. Additionally, yields of the desired metal-macrocycle which are substantially improved over those of the prior art can be achieved using the method of the instant invention.

An additional advantage which emerges out of the use of an organic-soluble metal ion source is that the metallated macrocycle can be considerably easier to isolate from the reaction mixture. For example, in the synthesis of a Lu(III)-texaphyrin complex using a Lu(III)-acetylacetonate in methanol, the complex formed between Lu(III) and the 2,4-diketone (2,4-pentanedione) is soluble in acetone, yet the Lu(III)-texaphyrin complex is acetone-insoluble. Thus, unreacted Lu(III)-acetylacetonate is quickly and easily separated from the desired product by washing the insoluble Lu(III)-texaphyrin with acetone. The simplicity of this method stands in contrast to those of the prior art which required contacting a solution of the crude product with a zeolite capable of entrapping the unreacted Lu(III) ion. At least two zeolite treatment cycles were required to obtain satisfactory removal of uncomplexed Lu(III). The zeolite treatments were time-consuming, requiring a period of stirring followed by filtration to remove the zeolite. Through the use of an organic-soluble metal ion source, the present invention avoids these difficulties.

Thus, in a first aspect, the invention provides a process for metallating an expanded porphyrin in an organic solvent, comprising:

(a) contacting a metal salt with a 2,4-dicarbonyl compound to form a metal-2,4-dicarbonyl complex between the 2,4-dicarbonyl compound and a metal ion derived from the metal salt; and (b) reacting the metal-2,4-dicarbonyl complex with the expanded porphyrin in the organic solvent to form a metallated expanded porphyrin.

The discovery extends to metal ions in general. Furthermore, the organic solvent may be any of a range of polar solvents. The metal salt to be used as a source of the metal ion can be selected such that the metal salt itself has low solubility in the organic solvent prior to complexation by the 2,4-dicarbonyl. The complexation permits the solubilization of the metal ion salt and affords access to metallated expanded porphyrins which cannot be synthesized in good yields using prior art methods.

Although the discovery extends to expanded porphyrins in general and also to metal ions in general, it is of particular interest as applied to texaphyrins and metal ions.

Thus, in a second aspect, the invention provides a process for metallating a texaphyrin precursor in an organic solvent, comprising:

(a) contacting a metal salt with a 2,4-dicarbonyl compound to form a metal-2,4-dicarbonyl complex between the 2,4-dicarbonyl compound and a metal ion derived from the metal salt; and (b) reacting the metal-2,4-dicarbonyl complex with the texaphyrin precursor in the organic solvent to give a metallated texaphyrin precursor.

In preferred embodiments of the above-described aspects of the invention, the metal-2,4-dicarbonyl complex is formed between a trivalent lanthanide ion and 2,4-pentanedione. In particularly preferred embodiments, the lanthanide ion is lutetium (III) or Gd(III) and the metallation of the expanded porphyrin is conducted in a $C_1$–$C_4$ alcohol such as methanol.

The characteristics and advantages of each of the aspects and embodiments of the invention will become apparent from the description that follows.

DETAILED DESCRIPTION OF THE INVENTION AND PREFERRED EMBODIMENTS

Macrocyclic metal ion complexing agents are known in the art and have found use as both diagnostic and therapeutic agents. Complexes between metal ions and macrocyclic ligands are used as MRI contrast agents, radiosensitizers, and as agents in PDT, radioimmunotherapy and other medical applications. Although the discussion below focuses on the texaphyrins as a representative example of a metal ion complexing expanded porphyrin, those of skill in the art will recognize that the present invention is broadly applicable to metal ion complexing expanded porphyrins in general. The use of texaphyrins as a representative example is intended neither to define nor limit the invention.

Texaphyrins and other expanded porphyrins, both prior to complexation and as metal complexes, are known in the art. Formula I is a representative generic formula for the $sp^3$ precursors to the texaphyrins:

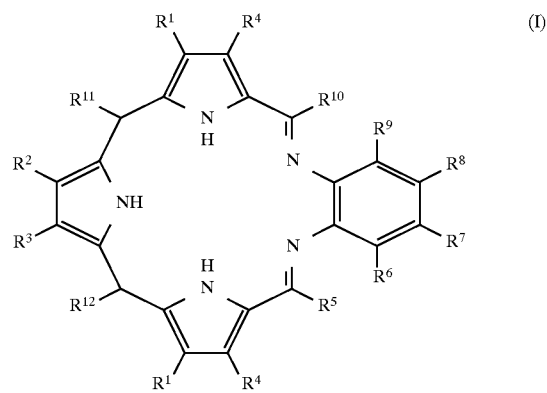

In one aspect of the invention, the $sp^3$ texaphyrin precursor is metallated using a metal-2,4-dicarbonyl complex. In preferred embodiments of this aspect of the invention, the texaphyrin precursor is oxidatively metallated using a metal-2,4-dicarbonyl complex. Oxidation can be effected by molecular oxygen, chemical oxidants or electrochemical methods.

Formula II is a representative generic formula for metal complexes (metallotexaphyrins) formed by metallation and oxidation of the expanded porphyrins of Formula I:

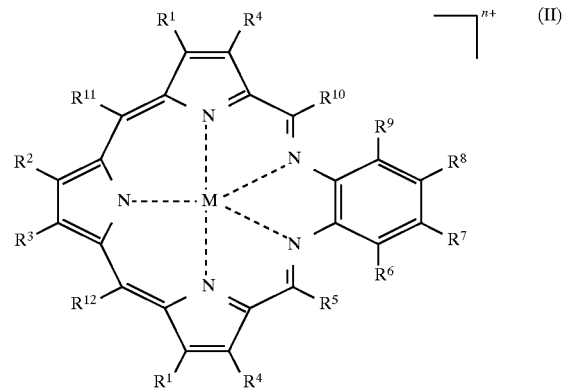

In these formulas:

each of $R^1$ through $R^4$ and $R^6$ through $R^9$ is independently a hydrogen atom, halide other than iodide, hydroxyl, alkyl, alkoxy, oligo(alkoxy), aryl, nitro, formyl, acyl, or saccharyl; or alkyl, alkoxy, or oligo(alkoxy) substituted with one or more of the following substituents: halo other than iodo, hydroxy, amino, carboxy, or carbamoyl;

$R^5$, $R^{10}$, $R^{11}$ and $R^{12}$ are each independently a hydrogen atom, alkyl, alkoxy, oligo(alkoxy), or aryl; or alkyl, alkoxy, or oligo(alkoxy) substituted with one or more of the following substituents: hydroxy, amino, carboxy (—$CO_2H$), or carbamoyl (—$C(O)NH_2$);

M is a monovalent, divalent or trivalent metal ion; and the formal charge "n" of the metallotexaphyrin is correspondingly zero, 1 or 2. Further charges may be introduced by ionized portions of any of the R-groups.

The terms used herein are defined as follows:

"Alkyl" denotes straight-chain, branched-chain, saturated and unsaturated groups. "Alkoxy" denotes "alkyl" with an added oxygen atom covalently linking the alkyl group to the remainder of the formula. Straight-chain, saturated groups are preferred for both alkyl and alkoxy. Further preferred alkyl and alkoxy groups are those containing 1 to 10 carbon atoms, with 1 to 5 carbon atoms per group particularly preferred.

"Oligo(alkoxy)" denotes 2 to 12 alkoxy groups covalently linked in either a linear or a branched configuration. Linear oligo(alkoxy) moieties have a structure such as —O—$(CH_2)_m$—O—$(CH_2)_m$—O—$(CH_2)_m$—... —O—$C_mH_{2m+1}$, where "m" is an integer, the same or different along the length of the chain. Branched moieties have two or more —O—$(CH_t)_m$—groups are bonded to a common third —O—$(CH_t)_m$—group, where "t" has a value which is independently selected from 0,1 and 2 for each $(CH_t)_m$ group. Linear configurations are preferred. Chains of 2 to 6 alkoxy groups (—O—$(CH_2)_m$—) are preferred. The individual alkoxy groups may be the same or different, and individual alkoxy groups preferably contain from 1 to 6 carbon atoms each, and most preferably from 1 to 3 carbon atoms each.

"Aryl" denotes groups formed from the six-carbon ring of benzene or the condensed six-carbon rings of other aromatic derivatives. Examples are phenyl, naphthyl, anthryl and phenanthryl. The preferred aryl group is phenyl.

"Acyl" denotes organic acid groups lacking the OH of the carboxyl group. Preferred acyl groups are those containing 2 to 12 carbon atoms, preferably 2 to 8, and most preferably 2 to 4. Examples are acetyl, propionyl, butyryl, and benzoyl.

"Saccharyl" denotes monosaccharides and other carbohydrate groups that can be either synthesized from or hydrolyzed to monosaccharides, the groups being formed by the elimination of the hydrogen atom bonded either to an oxygen atom or a carbon atom. Included within the term "saccharyl" are radicals of monosaccharides, disaccharides, and oligosaccharides, as well as open-chain forms of these groups and various derivatized forms. Examples are radicals formed from hexoses such as D-glucose, D-mannose, and D-galactose; pentoses such as D-ribose and D-arabinose, ketoses such as D-ribulose and D-fructose; disaccharides such as sucrose, lactose and maltose; derivatives such as acetals, amines and phosphorylated sugars, examples of amines being galactosamine, glucosamine, sialic acid and D-glucamine derivatives such as 1-amino-1-deoxysorbitol.

"Heterocyclic" is used herein to describe a saturated, aromatic or unsaturated non-aromatic group having a single ring or multiple condensed rings from 1–12 carbon atoms and from 1–4 heteroatoms selected from nitrogen, sulfur or oxygen within one or more of the rings. Such heterocycles are, for example, tetrahydrofuran, morpholine, piperidine, pyrrolidine, thiophene, pyridine, isoxazole, phthalimide, pyrazole, indole, furan, or benzo-fused analogues of these rings. Also encompassed within the term "heterocyclic" are substituted heterocycles.

"Halogen" is used herein to refer to fluorine, bromine, chlorine and iodine atoms.

"Hydroxy" is used herein to refer to the group —OH.

"Amino" is used to describe primary amines, —$NH_2$.

"Carboxy" denotes the group —COO(H), in either its acidic or anionic form.

"Cyano" is used to describe the group —CN, wherein the bond between carbon and nitrogen is a triple-bond.

"Alkylamino" denotes secondary and tertiary amines of the general formula —$NR_1R_2$ wherein one of $R_1$ and $R_2$ is hydrogen and the other is an alkyl group or $R_1$ and $R_2$ are the same or different alkyl groups.

"Independently" signifies that two or more of the groups immediately preceding the term are either identical or different, i.e., selection of one from the list following the term does not affect selection of the other(s).

"Substituted" encompasses both single and multiple substitutions, the latter including multiple substitutions by the same substituent as well as mixtures of different substituents.

In further preferred embodiments of the invention, $R^1$ is alkyl or hydroxyalkyl; $R^2$, $R^3$ and $R^4$ are alkyl; $R^5$, $R^6$, $R^9$, $R^{10}$, $R^{11}$ and $R^{12}$ are hydrogen atoms; $R^7$ and $R^8$ are independently a hydrogen atom, hydroxyalkyl, carboxyalkyl, carboxyalkoxy, hydroxyalkoxy, alkoxy or oligo(alkoxy). In still further preferred embodiments, $R^7$ and $R^8$ are independently a hydrogen atom, hydroxyalkoxy, carboxyalkoxy, alkoxy, or oligo(alkoxy).

The methods described herein are not limited to use with texaphyrins. These methods can be practiced with a variety of different macrocyclic compounds including, for example, natural and synthetic porphyrins, expanded porphyrins and polyazamacrocycles.

The metals represented by M include both paramagnetic and diamagnetic metals, the former being particularly useful for complexes used as MRI contrast agents, and the latter being particularly useful in photodynamic therapy. The use of either of these classes of metal ions is not intended to be limited by this generalization. Preferred metals are generally those having atomic numbers of 21–30 (inclusive), 39, 48, 49, 57–71 (inclusive, lanthanides), and 90–103 (inclusive, actinic), with oxidation states of 2 or 3. Of these, the ones having atomic numbers of 25, 48, 49, 39 or 57–71 (inclusive) are more preferred. Examples of such metals are chromium (III), manganese (II), manganese (III), iron (II), iron (III), cobalt (II), nickel (II), copper (II), indium (III), praseodymium (III), neodymium (III), samarium (III), gadolinium (III), terbium (III), dysprosium (III), holmium (III), europium (II), europium (III), erbium (III), lutetium (III), ytterbium (III), yttrium (III), cerium (III), thulium (III) and lanthanum (III).

In a still more preferred embodiment, the metal ion is yttrium (III) or a lanthanide ion. In an even more preferred embodiment, the metal ion is a lanthanide ion. Of the lanthanide ions, gadolinium (III), dysprosium (III) and lutetium (III) are the most preferred.

Examples of specific compounds that are presently preferred are those in which M is Gd(III), Y(III), Lu(III), Eu(III) or Dy(III); $R^1$ is 3-hydroxypropyl; $R^2$ and $R^3$ are ethyl; $R^4$ is methyl; $R^5$, $R^6$, $R^9$, $R^{10}$, $R^{11}$, and $R^{12}$ are hydrogen; and $R^7$ and $R^8$ are both —$O(CH_2)_3OH$ or —$O(CH_2CH_2O)_3CH_3$, or $R^7$ is hydrogen, $CH_3$ or $OCH_3$ and $R^8$ is —$O(CH_2CH_2O)_3CH_3$ or —$O(CH_2)_nCOOH$ where n is 1–3.

A wide variety of 2,4-dicarbonyl compounds can be used as the complexing agent for the metal ion in practicing this invention. Currently, a non-uniform nomenclature exists in the art for such 2,4-dicarbonyl compounds. For example, 2,4-diketones corresponding in structure to Formula III are named as 1,3-diketones, or alternatively, as 2,4-diketones. The scope of the invention is not intended to be limited by this aberration in the nomenclature and the only structural limitation placed on the 2,4-dicarbonyl compounds of use in the invention is that there be at least one carbon with at least one ionizable hydrogen atom located in a position between the two carbonyl functionalities. The method of this invention can be practiced with any 2,4-dicarbonyl incorporating the general structural motif shown in Formula (III).

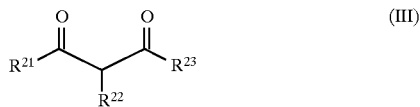

In Formula III, $R^{21}$, $R^{22}$ and $R^{23}$ are independently chosen and can be, for example, hydrogen, alkyl, substituted alkyl, aryl, acyl, heterocyclic, alkoxy, cyano, hydroxy, halide or amino groups. When the radical is a substituted alkyl group, the substituents are independently chosen from, for example, heterocycles, hydroxy, alkoxy, amino, alkylamino, carboxy, cyano and halogen. Also encompassed within the structure of Formula III are derivatives wherein either or both $R^{21}$ and $R^{23}$ are oxygen which bears a negative charge (i.e., the carbonyl moiety is a carboxylate) and which is associated with a positively charged counterion comprising a metal ion (e.g., $Li^+$, $Na^+$, $K^+$, $Ca^{+2}$, $Ba^{+2}$).

In a preferred embodiment of the invention $R^{21}$ and $R^{23}$ are $C_1$–$C_6$ alkyl groups or $C_1$–$C_6$ substituted alkyl groups and $R^{22}$ is H or an alkyl group. In a more preferred embodiment, $R^{21}$ and $R^{23}$ are $C_1$–$C_3$ alkyl groups and $R^{22}$ is H. In a still more preferred embodiment $R^{21}$ and $R^{23}$ are either unsubstituted or substituted methyl groups and $R^{22}$ is H.

The use of derivatives of 2,4-dicarboxylic acids such as, for example, malonic acid are within the scope of the instant invention. Thus, the 2,4-dicarbonyl compound can comprise diesters such as dimethyl- or diethyl-malonate, diamides such as malonamide, or dialdehydes such as malonaldehyde. Additional examples of 2,4-dicarbonyl compounds include, but are not limited to 1,3-acetonedicarboxylic acid, N-(acetoacetyl)glycine, o-acetoacetoluidide, acetoacetamide, acetoacetanilide, o-acetoacetanisidide, acetoacetic acid and ethyl acetoacetate. The above list is intended merely to offer examples of 2,4-dicarbonyl compounds of use in practicing the instant invention and is not intended to serve as a limitation on the range or identity of compounds of use in conjunction with this invention. Additional dicarbonyls which form organic solvent-soluble complexes with metal ions, and with lanthanides in particular will be apparent to those of skill in the art.

In certain preferred embodiments, the 2,4-dicarbonyl compound is a 2,4-diketone. 2,4-diketones of use in practicing the instant invention include, but are not limited to, acetylacetone, trifluoroacetylacetone, hexafluoroacetylacetone, thenoyltrifluoroacetone, 2,2,6,6-tetramethylheptane-3,5-dione, 1,1,1,5,5,6,6,7,7,7-decafluoro-2,4-heptanedione, 4,6-dioxoheptanoic acid, 3-ethyl-2,4-pentanedione and 5-methyl-1,3-hexanedione. Additionally, 2,4-diketones in which one of the hydrogens on the carbon between the two carbonyl groups is replaced with an alkyl (e.g. 2-methyl-1,3-hexanedione) or substituted alkyl can be used in the method of the invention. Ketones having more than 2 carbonyl groups within their framework such as 1-(3-(2,4-dioxopentyl)phenyl)pentane-2,4-dione (a tetraketone) and cyclic ketones such as 1,3-cyclohexanedione can also be used to practice the invention. In further preferred embodiments the 2,4-diketone is 2,4-pentanedione or a derivative thereof.

The appropriate 2,4-dicarbonyl compound in any particular case will be one that combines with the metal ion to form a complex that is substantially soluble in the solvent used for the expanded porphyrin metallation reaction. By "substantially soluble" is meant that the metal-2,4-dicarbonyl complex is sufficiently soluble in the chosen organic solvent that the reaction mixture is a homogenous solution at either the outset of the reaction or becomes a homogenous solution over the course of the reaction. "Substantially soluble" is intended to apply only to the metal-2,4-dicarbonyl complex and should not be assumed to preclude those reaction mixtures wherein the metallated expanded porphyrin, once formed, may precipitate out of solution.

Within the scope of the invention is the ability to adjust the solubility of the metal-2,4-dicarbonyl complex and the strength of the bond(s) between the 2,4-dicarbonyl and the metal ion. The solubility in organic solvent can be manipulated by varying the size, charge and hydrophobic/hydrophilic character of the 2,4-dicarbonyl. Similarly, by manipulating the electronic character of the substituents (i.e. $R^{21}$, $R^{22}$ and/or $R^{23}$) on the 2,4-dicarbonyl nucleus of Formula III, the strength of the bond between the 2,4-dicarbonyl and metal ion can be adjusted. For example, an electron-withdrawing substituent on the 2,4-dicarbonyl nucleus will reduce the charge concentration on the enolate oxygen of the 2,4-dicarbonyl resulting in a more weakly bonded metal-2,4-dicarbonyl complex. The opposite effect is expected from substituting the nucleus with an electron-releasing substituent. Thus, by judicious choice of the 2,4-dicarbonyl compound from the wide array of 2,4-dicarbonyl compounds useful in this invention, both the solubility and stability of the metal-2,4-dicarbonyl complex can be adjusted.

The 2,4-dicarbonyl compounds are known compounds that are readily available worldwide from chemical suppliers. Further, many 2,4-dicarbonyls which are not commercially available are readily accessible to those of skill in the art by well known synthetic procedures. For example, see ORGANIC SYNTHESIS: COLLECTED VOLUMES, Shriner, R. L., et al., Eds., John Wiley and Sons, New York, 1976 (see particularly, Index and more particularly Index at p. 262, listing 21 diketone syntheses), which is incorporated herein by reference. Certain preformed metal-2,4-dicarbonyl complexes are available commercially. For example, metal diketonates are commercially available. The use of commercially available metal-2,4-dicarbonyl complexes is also within the scope of the instant invention. Alternatively, metal-2,4-dicarbonyl complexes can be prepared by conventional methods known in the art. For example, general methods for preparing metal-2,4-diketonates are disclosed in Desreux, J. F., in LANTHANIDE PROBES IN LIFE, CHEMICAL AND EARTH SCIENCES. THEORY AND PRACTICE. Bünzli, J.-C. G, Ed., Elsevier, N.Y., 1989, pp. 43–64, and references therein, which are incorporated herein by reference.

The metal-2,4-dicarbonyl complex may be prepared in situ in the expanded porphyrin metallation mixture, or may be prepared separate from this metallation mixture. For example, when a metal-2,4-diketonate is utilized, the metal-2,4-diketonate can be synthesized in bulk, purified and stored until needed. When the metal-2,4-diketonate is prepared in a solvent which is incompatible with the expanded porphyrin metallation reaction, the solvent may be stripped off or otherwise removed or the metal-2,4-diketonate may be precipitated from the reaction mixture by addition of a solvent in which the metal- 2,4-diketonate is insoluble. Thus synthesized and isolated, the metal-2,4-diketonate is subsequently redissolved into the reaction medium for the metallation of the expanded porphyrin. In preferred embodiments, the metal-2,4-dicarbonyl complex is formed in situ by combining the metal salt and the 2,4-dicarbonyl in the solvent intended for the metallation reaction. After an incubation period, the expanded porphyrin is added directly to the solution of the metal-2,4-dicarbonyl complex.

The starting salt used as the source of the metal ion can be any salt that dissociates sufficiently in the presence of the 2,4-dicarbonyl to allow a complex between the metal ion and the 2,4-dicarbonyl to be formed. In preferred embodiments, the metal salt is a metal acetate, chloride, nitrate, oxide or sulfate. In further preferred embodiments the metal salts are lanthanide ion salts. In a particularly preferred embodiment, the metal salt is lutetium(III) acetate or gadolinium(III) acetate.

A variety of solvents can be used in the practice of this invention. The choice of solvent in any particular case will depend on the solubility of the expanded porphyrin, the metal ion, the source salt for the metal ion, and the metal-2,4-dicarbonyl complex. Selection of the solvent will be governed by various guidelines, including:

(1) The metal-2,4-dicarbonyl complex used is preferably soluble in the solvent before, during and after treatment with the expanded porphyrin;
(2) The unmetallated 2,4-dicarbonyl compound is preferably appreciably soluble following transfer of the metal ion to the expanded porphyrin;
(3) The unmetallated expanded porphyrin preferably is appreciably soluble in the selected solvent; and
(4) The solvent does not displace the 2,4-dicarbonyl of the intermediate metal-2,4-dicarbonyl complex to form a different complex which is unreactive with the expanded porphyrin.

The solvents will, in general, be polar solvents. For example alcohols, esters, ethers, amides, sulfoxides and ketones can be used in practicing the instant invention. Specific examples include methanol, ethanol, isopropanol, n-butanol, dimethyl sulfoxide, dimethyl formamide, tetrahydrofuran, acetone, ethylene glycol dimethyl ether, dioxane and mixtures of such solvents with each other and/or water. In preferred embodiments, the expanded porphyrin is a texaphyrin or a texaphyrin precursor and the solvent is an alcohol, with short chain alcohols such as $C_1$–$C_4$ alcohols being preferred. Particularly preferred are methanol and ethanol.

Sufficient 2,4-dicarbonyl compound is used to consume all or substantially all of the noncomplexed metal ion. In preferred embodiments, approximately one equivalent of the 2,4-dicarbonyl compound will be sufficient to rapidly convert the metal ion into the corresponding metal-2,4-dicarbonyl complex. In embodiments wherein the metal ion is supplied as a salt that is only partially soluble in the reaction medium, an excess of the 2,4-dicarbonyl compound can be used to encourage solubilization of the metal ion. The unreacted 2,4-dicarbonyl compound can be allowed to remain in the reaction mixture or it can be removed from the metal-2,4-dicarbonyl complex prior to reacting the metal-2, 4-dicarbonyl complex with the expanded porphyrin.

In preferred embodiments, the molar ratio of 2,4-dicarbonyl compound to metal ion will be from about 3.5:1.0 to about 0.1:1.0, and most preferably in the range of from about 1.5:1.0 to about 0.5:1.0.

The amount of metal-2,4-dicarbonyl complex that is used to react with the expanded porphyrin and to form the metallated expanded porphyrin can vary depending on the metal ion chosen, the expanded porphyrin, the concentrations of these components in the reaction mixture, and the reaction conditions. In most cases, however, best results will be achieved with a metal-2,4-dicarbonyl complex-to-expanded porphyrin molar ratio of from about 1.0:1.0 to about 3.0:1.0 and preferably from about 1.0:1.0 to about 1.5:1.0.

When conducted in organic solvents, the reaction between the metal-2,4-dicarbonyl complex and the expanded porphyrin can be performed under neutral or basic conditions. Basic conditions are most preferred when the expanded porphyrin contains ionizable groups which are involved in the complexation. Thus, bases which are soluble in the reaction medium (e.g. $R_3N$, $R_2NH$, $RNH_2$, etc.) may be added to ensure that the complexing groups remain unprotonated. Alternatively, bases which are substantially insoluble in the reaction mixture (e.g., $K_2CO_3$, $BaCO_3$) may be used.

Metallation of the expanded porphyrin can be conducted at any temperature between the boiling and freezing points of the reaction medium. The criteria used in choosing the reaction temperature will be the rate of expanded porphyrin metallation and the stability of the products and reactants at the chosen temperature. The preferred temperature is one that maximizes the rate of product formation while minimizing any decomposition of either products or reactants. Similar considerations apply to the reaction in which the metal-2,4-dicarbonyl complex is formed. Adequate results are generally obtained at temperatures which are between about 20° C. and about 80° C. In preferred embodiments wherein the reaction solvent is an alcohol, the expanded porphyrin metallation and formation of the metal-2,4-dicarbonyl complex reactions are run at the reflux temperature of the reaction solvent.

The reaction is permitted to continue for a period of time sufficient to allow transfer of the metal ion from the metal-2,4-dicarbonyl complex to the expanded porphyrin. The reaction can be assisted by agitation. In most cases, the reaction will be completed within fifteen hours, and reaction times of about six to about eight hours are preferred. In preferred embodiments utilizing texaphyrin precursors, the precursor is oxidized to a texaphyrin contemporaneous with the metallation reaction. Oxidation is effected by the use of molecular oxygen or chemical oxidizing agents. In preferred embodiments, molecular oxygen is bubbled into the reaction mixture during the metallation.

Isolation and purification of the desired product is achieved by conventional means such as, for example, evaporation, extraction, precipitation, crystallization, filtration, decantation, centrifugation, chromatography or a combination of such techniques. In embodiments wherein the metallated expanded porphyrin remains dissolved in the reaction medium, it can first be recovered by evaporation of the solvent or other conventional means. In preferred embodiments a solvent is available in which the 2,4- dicarbonyl and metal-2,4-dicarbonyl complex are soluble, yet in which the metal-expanded porphyrin is insoluble.

The following detailed examples are offered for illustrative purposes only.

EXAMPLES

Materials and Methods

The following materials and methods were used in each of the examples detailed below.

Materials

Lu(OAc)$_3$.xH$_2$O was obtained from Strem Chemicals, Newburyport, Mass., USA. Triethylamine, Arsenazo III and 2,4-pentanedione were obtained from Aldrich Chemical Company, St. Louis, Mo., USA. Methanol was obtained from J. T. Baker, Phillipsburg, N.J., USA and 4% N$_2$/96% O$_2$ was obtained from Air Liquide, Walnut Creek, Calif., USA. Reverse phase TLC plates (KC8F, 1.5×10 cm) were obtained from Whatman, Inc., Clifton, N.J., USA. LZY-54 zeolite was obtained from UOP Molecular Sieve Plant, Chickasaw, Ala., USA.

Methods

1. Lu (III)-expanded porphyin purity by HPLC

The purity of the expanded porphyrin was assessed using reverse-phase HPLC on a Prodigy ODS2 column. The column was 150×3.2 mm in size with a 5 $\mu$ particle size. The mobile phase was 72:28 100 mM ammonium acetate (pH 4.3):acetonitrile. The flow rate was 0.7 mL/min and the column effluent was monitored at 470 nm. The total run time was 28 min. Under these conditions, the Lu(III)-expanded porphyrin had a retention time of approximately 22 minutes.

2. Monitoring the course of the metallation reaction

The reaction was monitored for completeness using UV/vis spectroscopy. Briefly, an aliquot (one drop) of the reaction mixture was withdrawn, diluted with MeOH (4 mL) and the UV/vis spectrum was measured from 325–900 nm. The concentration of the UV/vis sample was adjusted with MeOH if necessary to maintain the maximum absorbance between 1.5 and 2.0. Glacial acetic acid (1 drop) was added to the cuvette, the mixture was agitated and the spectrum was measured as described above. When the ratio of the absorbance at 354 nm to that at 475 nm reached 0.24–0.26 the reaction was deemed to be complete.

3. Detecting the presence of uncomplexed metal ion

The presence of uncomplexed metal ion in the reaction mixture was assayed using reverse-phase thin layer chromatography (TLC). A sample of the reaction mixture was spotted onto a C$_8$-reverse-phase TLC plate and the plate was developed in 9:1 MeOH:acetic acid. After removal from the developing solvent, the plate was dried. The green-colored metallated expanded porphyrin migrated with the solvent front. The lower one-fourth of the plate is stained with a MeOH solution of Arsenazo III (0.4 mg/mL). A blue spot observed at the origin is indicative of free metal ion.

3. Elemental analysis

Elemental analyses (C, H, N, Lu$^{+3}$) were obtained from Schwarzkopf Microanalytical Laboratory, Woodside, N.Y., U.S.A.

Example 1

This example illustrates the prior art method for preparing a lutetium-texaphyrin complex from an sp$^3$ expanded porphyrin and lutetium acetate hydrate. The metallation is performed in MeOH and utilizes Lu(III) acetate as a Lu(III) source. Due to the low solubility of the metal salt in organic solvents, an excess of both the Lu(III) acetate and also of MeOH is required to achieve a satisfactory concentration of Lu(III) in solution. This reaction is characterized by lengthy reaction times (29 h) and it affords the final product in rather low yields (27%). The starting sp$^3$ expanded porphyrin is a texaphyrin precursor represented by Formula IV and the complex is represented by Formula V.

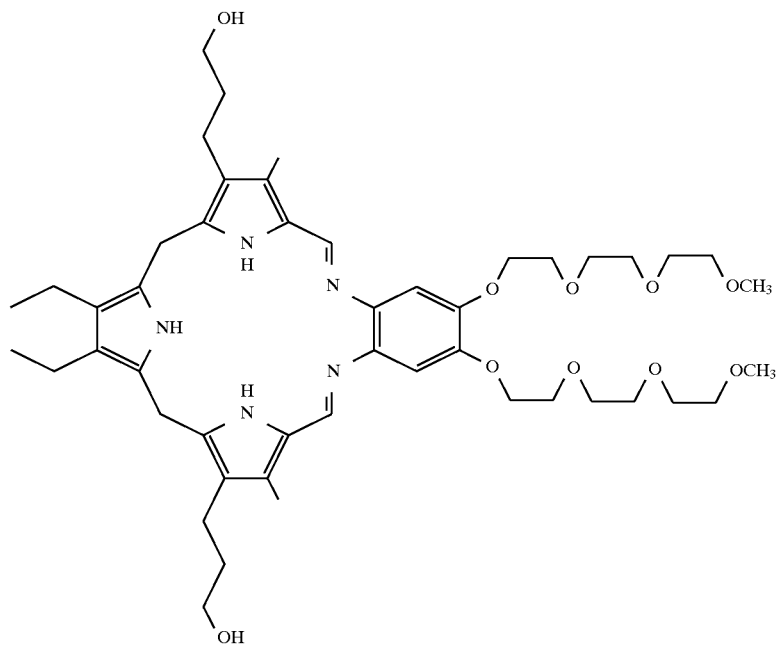

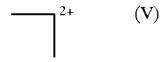

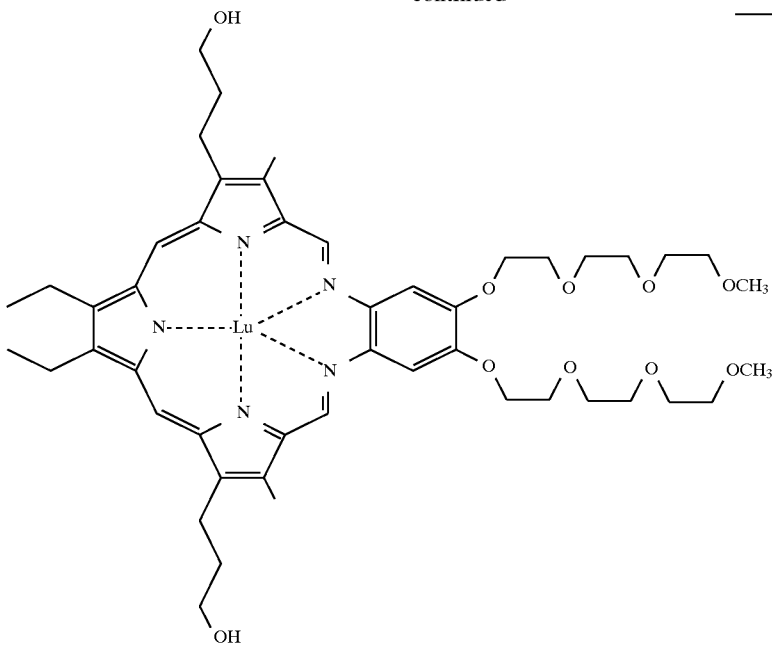

In a dry 3 L three-neck round-bottom flask, the expanded porphyrin (IV) (50 g, 55 mmol) was dissolved in MeOH (1500 mL). To this well-stirred, dark red solution was added lutetium (III) acetate (35.0 g, 82.1 mmol) and triethylamine (76 mL, 1 mole). The resulting suspension was heated to reflux. After 2 h at reflux, air was bubbled for 30 min into the suspension via a gas dispersion tube (flow rate=50 mL/min). During the next 27 hours, the suspension was maintained at reflux and air was intermittently bubbled through the mixture at a flow rate of 60 mL/min. The total time over which the air was introduced into the mixture was approximately 4 h. After 29 h, the reaction was deemed complete. The suspension was cooled to room temperature, filtered through a pad of CELITE® 545 and the solvent was removed under reduced pressure. The remaining dark-green solid was suspended in acetone (1600 mL) and stirred for 1 h at room temperature. The green solid was collected by filtration, washed with acetone (1000 mL) and dried in vacuo for several hours, yielding 38 g of crude Lu(III)-macrocycle. The crude Lu(III)-macrocycle was dissolved in MeOH (1400 mL) and this solution was stirred for 30 min. then filtered through a pad of CELITE® 545. Water (140 mL) and acetic acid washed LZY-54 zeolite (150 g) were added to the solution and the mixture was stirred by means of an overhead stirring apparatus for approximately 5 h. The zeolite was removed by filtration through Whatman #3 filter paper and rinsed with MeOH (200 mL). The filtrate and rinses were combined and concentrated to approximately 900 mL. This solution was passed through a column of AMBERLITE® IRA-904 anion exchange resin (acetate form, 2.0 cm×18 cm, 10–12 mL flow rate). The column was rinsed with MeOH (300 ml) and the rinse solution and eluent were combined and evaporated to dryness under reduced pressure. The resulting solid was suspended in acetone (600 mL), stirred 2 h, collected by filtration and washed with acetone (100 mL). The crude product was suspended in ethanol (650 mL) and the mixture was heated to reflux for 1 h. Once homogenous, the green solution was hot-filtered. The filtrate was allowed to cool slowly to room temperature, then placed in a freezer overnight to ensure complete crystallization. The crystallization mixture was stirred for 1 h at room temperature and the crystalline Lu(II)-texaphyrin was collected by filtration. The collected Lu(III)-texaphyrin was dried in vacuo for 24 h at room temperature and subsequently for 48 h at 45° C. to afford 17 g (27%) of the pure metallated Lu(III)-texaphyrin (V) as a dark green solid.

The metallated Lu(III)-texaphyrin (V) was analyzed by UV/vis spectroscopy, fast atom bombardment mass spectrometry (FAB MS), high resolution mass spectrometry (HRMS) and elemental analysis giving the following results:

UV/vis (MeOH) $\lambda$max (nm), (log e): 354 (4.33), 414 (4.67), 474 (5.10), 672 (sh), 732 (4.62).

FAB MS: $[M-OAc^-]^+$: m/e 1106.4

HRMS: $[M-OAc^-]^+$: m/e 1106.4330 (calc'd. for $[C_{48}H_{66}N_5O_{10}Lu(OAc)]^+$, 1106.4351).

| Elemental Analysis $[C_{48}H_{66}N_5O_{10}Lu](OAc)2H_2O$ | | |
|---|---|---|
| | Calculated | Found |
| C | 52.74 | 52.74 |
| H | 6.30 | 6.18 |
| N | 5.91 | 5.84 |

As can be seen from the above-detailed example, the prior art methods for metallating expanded porphyrins with lanthanide salts, particularly those of lutetium (III), in organic solvents require long reaction times and provide rather low yields. These results are thought to derive from the low solubility of the metal salt in the organic solvent. In the examples below are detailed the methods of the instant invention wherein using a metal complex which is soluble in an organic solvent provides advances over the prior art method; notably, the use of shortened reaction times and a two-fold increase in the yield of the desired product.

Example 2

This example demonstrates an embodiment of the invention in which the complex between 2,4-pentanedione and lutetium (III) is preformed in MeOH and subsequently combined with macrocycle (IV), an expanded porphyrin. The Lu(III) 2,4-pentanedione complex comprises a source of Lu(III) which is markedly more soluble in organic solvents than the precursor Lu(III) acetate. The solubility of the Lu(III) complex allows the reaction to be performed using only one equivalent of the Lu(III) source, yet affords a 2-fold increase in the yield (52% vs. 27%) of the Lu(III)-texaphyrin (V).

Lu(OAc)$_3$·xH$_2$O (1.856 g, 4.38 mmol), 2,4-pentanedione (0.449 mL, 4.37 mmol) and triethylamine (4.80 mL, 34.44 mmol) were combined in MeOH (40 mL). Macrocycle (IV) (4.008 g, 4.38 mmol) in MeOH (10 mL) was added and the solution was heated at reflux for 22 hours. 4% O$_2$/96% N$_2$, used as an oxidant, was sparged through the reaction mixture at a flow rate of approximately 16 mL/min for a total of 8 hours.

The reaction was allowed to cool to room temperature and the solvent was then removed under reduced pressure. The resulting residue was slurried in acetone (33 mL) and stirred for 1 h. The Lu(III)-texaphyrin (V) was collected by filtration and washed with acetone until the filtrate was practically colorless. The Lu(III)-texaphyrin was dissolved in MeOH (91 mL) and the solution was agitated on a rotary evaporator. Water (9 mL) and acetic acid washed zeolite (2.0 g) were added to the solution. Agitation was continued for 1 h. The zeolite was removed by filtration through #3 Whatman filter paper. Another portion of zeolite (2 g) was added to the filtrate and the mixture was agitated for 2 h and filtered. The filtrate was passed down a column of AMBERSEP® 900 anion exchange resin (acetate form; 1.5 cm×14 cm). The column was washed with approximately 1 bed volume of MeOH. The main eluent and wash solutions were combined and the volume was reduced by one-third under reduced pressure. The remaining MeOH solution was filtered through a 0.1 $\mu$ nylon filter. The filtered solution was evaporated to dryness under reduced pressure (a small amount of EtOH was added to form an azeotrope with any remaining H$_2$O) and the resulting residue was dried under high vacuum overnight affording 2.961 grams of the crude Lu(III)-texaphyrin.

The crude Lu(III)-texaphyrin (2.961 g) was dissolved in a mixture of ethanol (45 mL) and H$_2$O (0.45 mL) by refluxing under N$_2$ on an oil bath. After 1 h, the temperature of the solution was slowly reduced by ramping down the temperature of the oil bath to 30° C. in 10° C. increments over 7 h. After removing the oil bath, the mixture was allowed to stand at room temperature for 1 h, then cooled to 10° C. for 1 h. The crystals which formed were collected by filtration, washed with isopropyl alcohol and then acetone (20 mL). The recrystallized Lu(III)-texaphyrin was dried in vacuo (10 torr) overnight affording 2.673 g (52%) of the pure Lu(III)-texaphyrin (V).

The purity of the Lu(III)-texaphyrin was confirmed by HPLC and elemental analysis. The HPLC analysis demonstrated that the crystalline material was approximately 93 % pure. The elemental analysis of the product corresponded with the calculated values for the Lu(III)-texaphyrin (V).

Elemental Analysis
[C$_{48}$H$_{66}$N$_5$O$_{10}$Lu](OAc)2H$_2$O

|   | Calculated | Found | (Dried in vacuo) |
|---|---|---|---|
| C | 53.56 | 53.02 | 53.00 |
| H | 6.22 | 6.32 | 6.17 |
| N | 6.01 | 6.04 | 6.10 |
| Lu | 15.00 | 15.11 |   |

Example 3

This example illustrates that use of the Lu(III) 2,4-pentanedione complex in a dilute reaction mixture provides a 2-fold increase in the yield of a product which is purer than that obtained by the method outlined in Example 1. This example further shows that the Lu(III) 2,4-pentanedione complex provides a useful Lu(III) ion source even when highly diluted. The increased dilution of the Lu(III) source does not require correspondingly increased reaction times to achieve a high yield of the pure metallated Lu(III)-texaphyrin.

Lu(OAc)$_3$·xH$_2$O (0.55 g, 1.30 mmol), 2,4-pentanedione (0.133 mL, 1.30 mmol) and triethylamine (1.2 mL, 8.61 mmol) were combined in MeOH (55 mL). The mixture was stirred until the lutetium salt was completely dissolved. Macrocycle (IV) (1.00 g, 1.09 mmol) was added and the solution was heated at reflux, under a 4% O$^2$/96% N$_2$ atmosphere for 22 h.

The reaction was allowed to cool to room temperature and the solvent was then removed under reduced pressure. The resulting residue was slurried in acetone (20 mL) and stirred for 30 min. The Lu(III)-texaphyrin was collected by filtration and washed with acetone until the filtrate was practically colorless. The Lu(III)-texaphyrin was dissolved in MeOH (29 mL). Water (2.9 mL) and acetic acid washed zeolite (3.0 g) were added to the solution and the mixture was agitated on a rotary evaporator for 1 h. The zeolite was removed by filtration through #3 Whatman filter paper and the collected zeolite was washed with MeOH. The filtrate and wash were combined and the solution was again treated with acetic acid washed zeolite, agitated for 7 h and filtered. The filtrate was passed down a column of AMBERSEP® 900 anion exchange resin (acetate form; 1.5 cm×15 cm). The column was washed with approximately 1–2 bed volumes of MeOH. The main eluent and wash solutions were combined and evaporated to dryness under reduced pressure. The residue was redissolved into a minimum amount of MeOH and the solution was filtered through a 0.2 $\mu$ teflon syringe filter. The filtered solution was evaporated to dryness under reduced pressure and the resulting residue was dried under high vacuum for 10 h affording 0.8996 g of the crude Lu(III)-texaphyrin.

The crude Lu(III)-texaphyrin (0.8996 g) was dissolved in a mixture of ethanol (14 mL) and H$_2$O (0.14 mL) by refluxing under N$_2$ for approximately 1 h. The resulting solution was allowed to cool slowly to room temperature during which time crystals of the Lu(III)-texaphyrin separated from the solution. The crystals were collected by filtration, washed with isopropyl alcohol and then acetone. The recrystallized Lu(III)-texaphyrin was dried under vacuum (10 torr) overnight affording 0.734 g (58%) of the pure metallated Lu(III)-texaphyrin (V).

The purity of the Lu(III)-texaphyrin was confirmed by HPLC and elemental analysis. HPLC analysis demonstrated that the crystalline material was approximately 92.24% pure.

The elemental analysis corresponded to the values calculated for the Lu(III)-texaphyrin (V).

Elemental Analysis
[C$_{48}$H$_{66}$N$_5$O$_{10}$Lu](OAc)2H$_2$O

|    | Calculated | Found  | (Dried in vacuo) |
|----|------------|--------|------------------|
| C  | 53.56      | 52.75  | 52.49            |
| H  | 6.22       | 6.71   | 6.87             |
| N  | 6.01       | 5.88   | 6.14             |
| Lu | 15.00      | 15.05  |                  |
| Cl |            | <0.1   |                  |

Example 3 demonstrates that the Lu(III) 2,4-pentanedione complex provides a useful source of the Lu(III) ion even when present in the reaction mixture at fairly low concentrations. Even at low concentrations of the soluble Lu(III) source, increased reaction times are not necessary to achieve higher yields than are afforded by the prior art method.

Example 4

This example illustrates the utility of the Lu(III) 2,4-pentanedione complex at concentrations which are intermediate to those described in Examples 2 and 3. In the present example, the concentration of the Lu(III) complex is approximately one-half that of the concentration in Example 2 and 2-fold greater than the concentration in Example 3. Similar to the results obtained in the above examples, use of approximately one equivalent of this Lu(III) source provides a higher yield of a pure metallated Lu(III)-texaphyrin than is obtained using the prior art method.

Lu(OAc)$_3$.xH$_2$O (0.927 g, 2.19 mmol), 2,4-pentanedione (0.225 mL, 2.19 mmol) and triethylamine (2.40 mL, 17.22 mmol) were combined in MeOH (50 mL). The mixture was stirred until the lutetium salt was completely dissolved. Macrocycle (IV) (1.99 g, 2.18 mmol) was added and the solution was heated at reflux, under a 4% O$_2$/96% N$_2$ atmosphere for 18 h.

The reaction was allowed to cool to room temperature and the solvent was then removed under reduced pressure. The resulting residue was slurried in acetone (20 mL) and stirred for 30 min. The Lu(III)-texaphyrin was collected by filtration and washed with acetone until the filtrate was practically colorless. The expanded porphyrin was dissolved in MeOH (50 mL) and H$_2$O (5 mL). Acetic acid-washed zeolite (4.0 g) was added to the solution and the mixture was agitated on a rotary evaporator for 30 min. The zeolite was removed by filtration through #3 Whatman filter paper and the collected zeolite was washed with MeOH. The filtrate and wash were combined and the solution was again treated with acetic acid washed zeolite (4.0 g), agitated for 30 minutes and filtered. The filtrate was passed down a column of AMBERSEP® 900 anion exchange resin (acetate form; 1.5 cm×14 cm). The column was washed with approximately 1 bed volume of MeOH. The main eluent and wash solutions were combined and evaporated to dryness under reduced pressure and the resulting residue was dried in vacuo overnight affording 1.738 grams of the crude Lu(III)-texaphyrin.

The crude Lu(II)-texaphyrin (1.738 g) was dissolved in ethanol (26 mL) and water (0.260 mL) by refluxing under N$_2$. The resulting solution was allowed to cool slowly to room temperature during which time crystals of the Lu(III)-texaphyrin separated from the solution. The crystals were collected by filtration, washed with isopropyl alcohol and dried under vacuum (10 torr) overnight affording 1.59 g (63%) of the pure Lu(III)-texaphrin (V).

The purity of the Lu(III)-expanded porphyrin was confirmed by HPLC and elemental analysis. HPLC analysis demonstrated that the crystalline material was approximately 93% pure. The elemental analysis corresponded to the values calculated for the Lu(III)-texaphyrin.

Elemental Analysis
[C$_{48}$H$_{66}$N$_5$O$_{10}$Lu](OAc)2H$_2$O

|    | Calculated | Found | (Dried in vacuo) |
|----|------------|-------|------------------|
| C  | 53.56      | 52.96 | 53.01            |
| H  | 6.22       | 6.34  | 6.42             |
| N  | 6.01       | 5.82  | 6.04             |
| Lu | 15.00      | 15.04 |                  |

Similar to Examples 2 and 3 above, Example 4 demonstrates that the Lu(III) 2,4-pentanedione complex provides a useful source of the Lu(III) ion which is soluble in organic solvents.

Example 5

Similar to Example 4, this example illustrates the usefulness of the Lu(III) 2,4-pentanedione complex at concentrations which are intermediate to those described in Examples 2 and 3. Use of this intermediate concentration provides a high yield of a pure final product and serves to further establish that the organic-soluble Lu(III) source of the invention is useful over a range of concentrations.

Lu(OAc)$_3$.xH$_2$O (1.393 g, 3.28 mmol), 2,4-pentanedione (0.337 mL, 3.28 mmol) and triethylamine (3.60 mL, 25.83 mmol) were combined in MeOH (45 mL). Macrocycle (IV) (3.00 g, 3.28 mmol) and MeOH (5 mL) were added and the solution was heated at reflux, under a 4% O$_2$/96% N$_2$ atmosphere for 12 h.

The reaction was allowed to cool to room temperature and the solvent was then removed under reduced pressure. The resulting residue was slurried in acetone (25 mL) and stirred for 1.5 h. The Lu(III)-texaphyrin was collected by filtration and washed with acetone until the filtrate was practically colorless. The collected solid was dried in vacuo affording 2.299 g of the crude metallated Lu(III)-texaphyrin. To the Lu(III)-texaphyrin was added MeOH (66 mL) and the resulting mixture was agitated on a rotary evaporator. H$_2$O (6.6 mL) was added and the agitation was continued until the Lu(III)-texaphyrin was largely dissolved. Acetic acid washed zeolite (4.0 g) was added to the solution and the mixture was agitated for 1.5 h. The zeolite was removed by filtration through #3 Whatman filter paper and the collected zeolite was washed with MeOH. The filtrate and wash were combined and the solution was again treated with acetic acid washed zeolite (4.0 g), agitated for 1 h and filtered. The filtrate was passed down a column of AMBERSEP® 900 anion exchange resin (acetate form; 1.5 cm×13 cm). The column was washed with approximately 2 bed volumes of MeOH. The main eluent and wash solutions were combined and filtered through a 0.2$\mu$ nylon filter. The filtrate was evaporated to dryness under reduced pressure and the resulting residue was dried in vacuo overnight affording 2.137 grams of the crude Lu(II)-texaphyrin.

The crude Lu(III)-texaphyrin (2.137 g) was dissolved in ethanol (32 mL) and water (0.32 mL) by refluxing the mixture under N$_2$ on an oil bath. The resulting solution was allowed to cool slowly to room temperature by ramping the temperature of the oil bath down in 10° C. increments. The Lu(III)-texaphyrin began to crystallize at 60° C. After reaching room temperature, the mixture was cooled to 10° C. for 30 min. The crystals were collected by filtration, washed with isopropyl alcohol. The recrystallized Lu(III)-texaphyrin was dried under vacuum (10 torr) overnight affording 1.955 g (51%) of the pure Lu(III)-texaphyrin (V).

The purity of the Lu(III)-texaphyrin was confirmed by HPLC and elemental analysis. HPLC analysis demonstrated that the crystalline material was approximately 92–93% pure. The elemental analysis corresponded to the values calculated for the Lu(III)-texaphyrin (V).

Elemental Analysis
[$C_{46}H_{66}N_5O_{10}Lu$](OAc)2H$_2$O

|    | Calculated | Found | (Dried in vacuo) |
|----|-----------|-------|------------------|
| C  | 53.56     | 52.73 | 53.16            |
| H  | 6.22      | 6.34  | 6.24             |
| N  | 6.01      | 6.01  | 6.12             |
| Lu | 15.00     | 14.92 |                  |

Similar to Examples 2, 3 and 4 above, Example 5 demonstrates that the Lu(III) 2,4-pentanedione complex provides a useful source of the Lu(III) ion which is soluble in organic solvents.

Example 6

In this final example, it is demonstrated that the use of the intermediate 2,4-diketone complex permits the use of reaction times which are 3–4-fold shorter than the method of the prior art, while affording a yield of the desired Lu(III)-texaphyrin which is 2-fold higher. In addition, the purification of the metallated Lu(III)-texaphyrin is simplified. Treating the crude product with a zeolite to remove uncomplexed Lu(III) ions, as in the prior examples, is eliminated and shown to be unnecessary. The solubility of the Lu(III)-2,4-pentanedione complex in acetone allows the Lu(III) which is not bound to the expanded porphyrin to be washed away from the desired product.

Lu(OAc)$_3$.xH$_2$O (0.929 g, 2.19 mmol), 2,4-pentanedione (0.225 mL, 2.19 mmol) and triethylamine (2.4 mL, 17 mmol) were combined in MeOH (50 mL). The mixture was stirred until the lutetium salt was completely dissolved. Macrocycle (IV) (2.00 g, 2.19 mmol) was added and the solution was heated at reflux, under a 4% $O^2$/96% $N_2$ atmosphere for 6 h.

The reaction was allowed to cool to room temperature and the solvent was then removed under reduced pressure. The resulting residue was slurried in acetone (25 mL) and stirred for 1 h. The Lu(III)-texaphyrin was collected by filtration and washed with acetone until the filtrate was practically colorless. The Lu(III)-texaphyrin was dissolved in MeOH (50 mL) and was passed down a column of AMBERSEP® 900 anion exchange resin (acetate form; 1.5 cm×17 cm). The column was washed with approximately 1 bed volume of MeOH. The main eluent and wash solutions were combined and the solution was filtered through a 0.2μ nylon filter. The filtered solution was evaporated to dryness under reduced pressure and the resulting residue was dried in vacuo overnight affording 1.719 g of the crude Lu(III)-texaphyrin.

The crude Lu(III)-texaphyrin (1.719 g) was dissolved in ethanol (26 mL) and H$_2$O (0.26 mL) by refluxing under N$_2$. After 2 h at reflux EtOH (2 mL) and H$_2$O (0.020 mL) were added. The resulting solution was allowed to cool slowly to room temperature during which time crystals of the Lu(III)-texaphyrin separated from the solution. The crystals were collected by filtration, washed with isopropyl alcohol and dried under vacuum (10 torr) for several hours affording 1.50 g (62%) of the pure Lu(III)-texaphyrin (V).

Example 6 demonstrates that the Lu(III) 2,4-pentanedione complex provides a useful source of the Lu(III) ion which is soluble in organic solvents. Further, this solubility can be exploited to both reduce the reaction time for metallation and to simplify the purification of the metallated Lu(III)-texaphyrin.

Taken together, the examples detailed above demonstrate that the method of the invention provides a metal ion source having a solubility in organic solvents which is significantly enhanced relative to the solubility of the simple metal salts of the prior art. The enhanced solubility allows the reaction to be run at a higher reactant concentration which in turn decreases the overall reaction time necessary to effect a satisfactory conversion of the reactants to the desired metallated texaphyrin. Additionally, similarly high yields are obtained even when the metal source is dilute. The dilute nature of the metal source does not necessitate increased reaction time. In addition, the examples demonstrate that the instant invention is operable over a range of reactant concentrations and also affords the metallated texaphyrin in yields which are approximately two-fold greater than that obtained using the prior art method. Furthermore, it has been demonstrated that the use of an organic-soluble metal ion source simplifies the purification protocol.

The foregoing is offered primarily for purposes of illustration. It will be readily apparent to those skilled in the art that the materials, proportions, procedural steps and other parameters of the formulation and its use may be further modified or substituted in various ways without departing from the spirit and scope of the invention.

What is claimed is:

1. A process for metallating an expanded porphyrin in an organic solvent, comprising:

(a) contacting a metal salt with a 2,4-dicarbonyl compound to form a metal-2,4-dicarbonyl complex between said 2,4-dicarbonyl compound and a metal ion derived from said metal salt; and (b) reacting said metal-2,4-dicarbonyl complex with said expanded porphyrin in said organic solvent to form a metallated expanded porphyrin.

2. A process in accordance with claim 1 in which said expanded porphyrin is a member selected from the group consisting of texaphyrins and texaphyrin precursors.

3. A process in accordance with claim 1 in which said 2,4-dicarbonyl compound and said metal salt are contacted in a molar ratio of from about 3.5:1.0 to about 0.1:1.0.

4. A process in accordance with claim 1 in which said 2,4-dicarbonyl compound and said metal salt are contacted in a molar ratio of from about 1.5:1.0 to about 0.5:1.0.

5. A process in accordance with claim 1 in which said metal salt comprises a lanthanide ion.

6. A process in accordance with claim 5 in which said lanthanide ion is a member selected from the group consisting of lutetium (III), dysprosium(III), and gadolinium (III).

7. A process in accordance with claim 1 in which said 2,4-carbonyl compound has the formula:

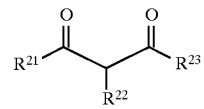

wherein:
R$^{21}$ is a member selected from the group consisting of heterocycles, hydroxy, alkoxy, amino, alkylamino, C$_1$–C$_6$ alkyl and C$_1$–C$_6$ alkyl substituted with one or more substituents independently selected from the group consisting of heterocycles, hydroxy, alkoxy, amino, alkylamino, carboxy, cyano and halogen;
R$^{22}$ is selected from the group consisting of H and C$_1$–C$_6$ alkyl; and
R$^{23}$ is a member selected from the group consisting of heterocycles, hydroxy, alkoxy, amino, alkylamino, C$_1$–C$_6$ alkyl and C$_1$–C$_6$ alkyl substituted with one or more substituents independently selected from the group consisting of heterocycles, hydroxy, alkoxy, amino, alkylamino, carboxy, cyano and halogen.
8. A process in accordance with claim 7 in which:
R$^{21}$ is a member selected from the group consisting of heterocycles, hydroxy, alkoxy, amino, alkylamino, C$_1$–C$_3$ alkyl and C$_1$–C$_3$ alkyl substituted with one or more substituents independently selected from the group consisting of heterocycles, hydroxy, alkoxy, amino, alkylamino, carboxy, cyano and halogen;
R$^{22}$ is H; and
R$^{23}$ is a member selected from the group consisting of heterocycles, hydroxy, alkoxy, amino, alkylamino, C$_1$–C$_3$ alkyl and C$_1$–C$_3$ alkyl substituted with one or more substituents independently selected from the group consisting of heterocycles, hydroxy, alkoxy, amino, alkylamino, carboxy, cyano and halogen.
9. A process in accordance with claim 7 in which:
R$^{21}$ is a member selected from the group consisting of is a member selected from the group consisting of heterocycles, hydroxy, alkoxy, amino, alkylamino, methyl and methyl substituted with one or more substituents independently selected from the group consisting of heterocycles, hydroxy, alkoxy, amino, alkylamino, carboxy, cyano and halogen;
R$^{22}$ is H; and
R$^{23}$ is a member selected from the group consisting of is a member selected from the group consisting of heterocycles, hydroxy, alkoxy, amino, alkylamino, methyl and methyl substituted with one or more substituents independently selected from the group consisting of heterocycles, hydroxy, alkoxy, amino, alkylamino, carboxy, cyano and halogen.
10. A process for metallating a texaphyrin precursor in an organic solvent, comprising:
(a) contacting a metal salt with a 2,4-dicarbonyl compound to form a metal-2,4-dicarbonyl complex between said 2,4-dicarbonyl compound and a metal ion derived from said metal salt; and
(b) reacting said metal-2,4-dicarbonyl complex with said texaphyrin precursor in said organic solvent to give a metallated texaphyrin precursor; and
(c) oxidizing said texaphyrin precursor to a texaphyrin-metal complex.
11. A process in accordance with claim 10 in which said 2,4-dicarbonyl compound is a 2,4-diketone.
12. A process in accordance with claim 10 in which said organic solvent is a polar organic solvent.
13. A process in accordance with claim 10 in which said organic solvent is a C$_1$–C$_4$ alcohol.
14. A process in accordance with claim 10 in which said metal salt is a member selected from the group consisting of salts of yttrium(III), dysprosium(III), lutetium (III) and gadolinium(III).
15. A process in accordance with claim 10 in which said metal salts comprise an anion selected from the group consisting of acetate, chloride, nitrate, oxide and sulfate.

16. A process in accordance with claim 10 in which said texaphyrin-metal complex is:

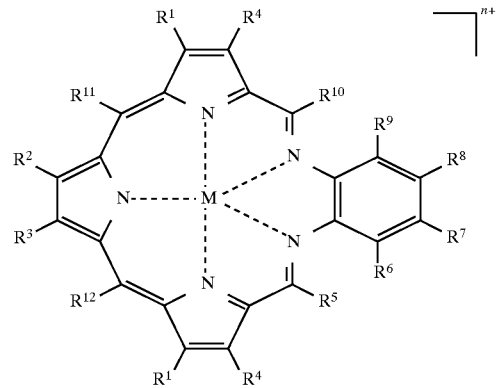

in which:
each of R$^1$ through R$^4$ and R$^6$ through R$^9$ is independently a member selected from the group consisting of hydrogen, halide other than iodide, hydroxyl, alkyl, alkoxy, oligo(alkoxy), aryl, nitro, formyl, acyl, saccharyl, and alkyl, alkoxy, and oligo(alkoxy) substituted with one or more of the following substituents: halo other than iodo, hydroxy, amino, carboxy, and carbamoyl;
R$^5$, R$^{10}$, R$^{11}$ and R$^{12}$ are each independently a member selected from the group consisting of hydrogen, alkyl, alkoxy, oligo(alkoxy), aryl, and alkyl, alkoxy, or oligo (alkoxy) substituted with one or more of the following substituents: hydroxy, amino, carboxy, and carbamoyl;
M is a member selected from the group consisting of monovalent, divalent and trivalent metal ions; and
n is zero, 1 or 2.
17. A process in accordance with claim 16 in which:
R$^1$ is hydroxyalkyl; R$^2$, R$^3$ and R$^4$ are alkyl;
R$^5$, R$^6$, R$^9$, R$^{10}$, R$^{11}$ and R$^{12}$ are hydrogen atoms;
R$^7$ and R$^8$ are independently a member selected from the group consisting of hydrogen, hydroxyalkyl, carboxyalkyl, carboxyalkoxy, hydroxyalkoxy, alkoxy and oligo(alkoxy);
M is a member selected from the group consisting of chromium (III), manganese (II), manganese (III), iron (II), iron (III), cobalt (II), nickel (II), copper (II), indium (III), praseodymium (III), neodymium (III), samarium (III), gadolinium (III), terbium (III), dysprosium (III), holmium (III), europium (II), europium (III), erbium (III), lutetium (III), ytterbium (III), yttrium (III), cerium (III), thulium (III) and lanthanum (III); and
n is 1 or 2.
18. A process in accordance with claim 16 in which:
R$^7$ and R$^8$ are independently a member selected from the group consisting of hydrogen, carboxyalkoxy, hydroxyalkoxy, alkoxy and oligo(alkoxy);
M is a member selected from the group consisting of yttrium (III), gadolinium (III), terbium (III), dysprosium (III), europium (II), europium (III), erbium (III), and lutetium (III); and
n is 1 or 2.
19. A process in accordance with claim 18 in which:
M is a member selected from the group consisting of gadolinium (III) and lutetium (III); and
n is 2.
20. A process in accordance with claim 10 in which said texaphyrin-metal complex is:

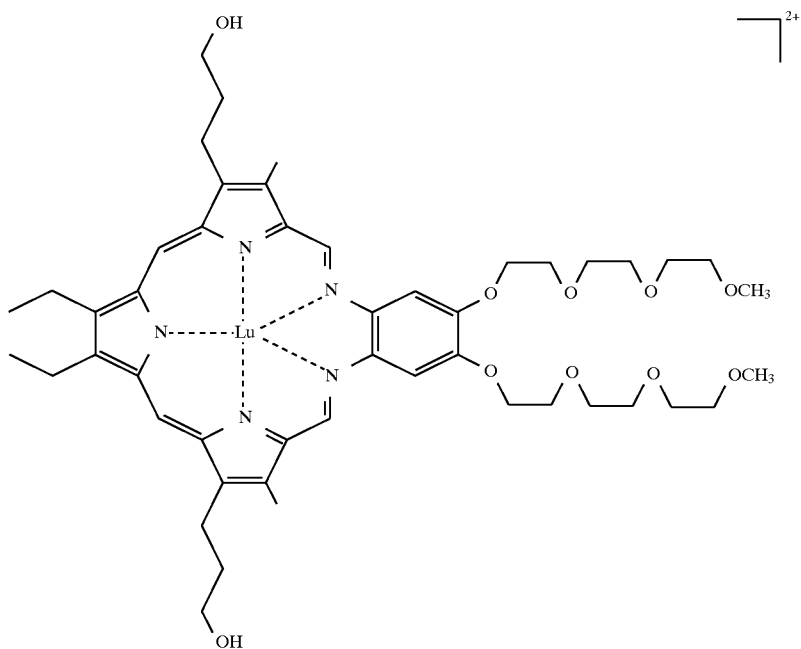
* * * * *